(12) United States Patent
Haskel et al.

(10) Patent No.: US 7,403,592 B1
(45) Date of Patent: Jul. 22, 2008

(54) DIGITAL LOCK-IN DETECTION OF SITE-SPECIFIC MAGNETISM IN MAGNETIC MATERIALS

(75) Inventors: Daniel Haskel, Naperville, IL (US); Jonathan C. Lang, Naperville, IL (US); George Srajer, Oak Park, IL (US)

(73) Assignee: The United States of America as represented by the Department of Energy, Washington, DC (US)

( * ) Notice: Subject to any disclaimer, the term of this patent is extended or adjusted under 35 U.S.C. 154(b) by 231 days.

(21) Appl. No.: 11/447,511

(22) Filed: May 31, 2006

(51) Int. Cl.
*G01N 23/00* (2006.01)
(52) U.S. Cl. .......................................... 378/71; 378/70
(58) Field of Classification Search ............. 378/70–73, 378/82–84, 86, 88–90, 106, 107, 113, 114, 378/210
See application file for complete search history.

(56) References Cited

U.S. PATENT DOCUMENTS

| | | | | |
|---|---|---|---|---|
| 4,165,937 | A * | 8/1979 | Murayama et al. | 356/319 |
| 2002/0051999 | A1 * | 5/2002 | Sepetov et al. | 435/7.1 |
| 2004/0141887 | A1 * | 7/2004 | Mainquist et al. | 422/102 |
| 2005/0067566 | A1 * | 3/2005 | Koshikawa et al. | 250/306 |

OTHER PUBLICATIONS

Funk, et al., X-ray magnetic circular dichroism—a high energy probe of magnetic properties, available online Oct. 27, 2004, Elsevier Science, published in print in Coordination Chemistry Reviews, 2005, vol. 249, p. 3-30.*

Keavney et al., Characterizing Nanostructured Magnetic Materials with Photonic Probes, Jun. 2000, JOM, vol. 52, No. 6, presented online at http://www.tms.org.pubs/journals/JOM/0006/Keavney/Keavney-0006.html. in 2000.*

Stohr et al., Magnetic properties of transition-metal multilayers studied with x-ray magnetic circular dichroism spectroscopy, 1998, IBM Journal of Research and Development, vol. 42, No. 1, pp. 1-13.*

* cited by examiner

*Primary Examiner*—Edward J. Glick
*Assistant Examiner*—Anastasia Midkiff
(74) *Attorney, Agent, or Firm*—Bradley L. Smith; Daniel Park; Paul A. Gottlieb

(57) ABSTRACT

The polarization and diffraction characteristics of x-rays incident upon a magnetic material are manipulated to provide a desired magnetic sensitivity in the material. The contrast in diffracted intensity of opposite helicities of circularly polarized x-rays is measured to permit separation of magnetic signals by element type and by atomic environment. This allows for the direct probing of magnetic signals from elements of the same species in nonequivalent atomic environments to better understand the behavior and characteristics of permanent magnetic materials. By using known crystallographic information together with manipulation of the polarization of x-rays having energies tuned near element-specific electronic excitations and by detecting and comparing the incident and diffracted photons at the same frequency, more accurate magnetic measurements can be made over shorter observation periods.

16 Claims, 2 Drawing Sheets

DIGITAL LOCK-IN DETECTION OF SITE-SPECIFIC MAGNETISM IN MAGNETIC MATERIALS

CONTRACTUAL ORIGIN OF THE INVENTION

The United States Government has rights in this invention pursuant to Contract No. W-31-109-ENG-38 between the U.S. Department of Energy and the University of Chicago.

FIELD OF THE INVENTION

This invention relates to a method and apparatus for detecting and measuring the behavior and characteristics of magnetic materials with very high resolution and accuracy.

BACKGROUND OF THE INVENTION

Magnetic materials are key components in a large number of technologies and devices such as car starters and alternators, microwave bandpass filters, and insertion devices for synchrotron radiation sources. Permanent magnets are an important class of magnetic materials and are defined as materials that retain a high degree of magnetization after a magnetizing field is removed. The amount of magnetic energy stored per the material's unit volume has increased ten-fold in the past few years due to technological progress in the synthesis of modern permanent magnets which feature rare-earth atomic constituents. This has allowed miniaturization of permanent magnets and increased versatility in their use. The resulting complex artificial structures, however, feature not only more than one type of magnetic atom, but atoms of the same species in different atomic environments. The simultaneous presence of rare-earth constituents in dissimilar crystal sites, or atomic environments, hinders our ability to understand their individual magnetic contributions by means of current detection methods. Not being able to fully understand existing materials inhibits the ability to develop new generations of permanent magnetic materials with improved performance in areas such as magnetic hardness (stability against demagnetizing fields) which are dictated by the interaction of magnetic moments with the local crystalline environment. Previous attempts to understand these properties have used established techniques such as Mossbauer spectroscopy and neutron diffraction. More recently, x-ray magnetic circular dichroism has also been used to detect and measure these and other characteristics of magnetic materials.

The main limitation of the neutron diffraction technique is that it probes all magnetic elements simultaneously. In the case of modern high-strength magnets, the majority of the magnetic atoms in the structure are transition metal atoms, such as Iron, while only a minority are rare-earth type. The magnetic hardness, however, is dominated by the minority rare-earth atoms. Understanding and improving magnetic hardness requires accurate detection of magnetic signals from these rare-earth atoms only. This is not possible using neutron diffraction. Finally, x-ray magnetic circular dichroism can separate magnetic contributions by element type, but cannot separate contributions from the same element in nonequivalent crystal sites or atomic environments. Only in special circumstances, where absorption thresholds between atoms in nonequivalent sites are large enough (vary rare), can this technique yield the information needed. In summary, none of the methods briefly discussed above, even when taken together, have been able to provide a complete understanding of the way in which modern permanent magnetic materials function and behave.

OBJECTS AND SUMMARY OF THE INVENTION

Accordingly, it is an object of the present invention to provide an improved method and apparatus for detecting and measuring the behavior and characteristics of magnetic materials.

It is another object of the present invention to provide for the use of x-ray magnetic circular dichroism to measure magnetic signals from different magnetic elements in a material, and magnetic signals of like elements present in nonequivalent crystal sites or atomic environments of a magnetic material.

A further object of the present invention is to determine the magnetic characteristics of individual atoms in permanent magnetic materials as determined by the interaction of the atom's magnetic moment with its local crystalline environment.

The present invention provides a way to directly detect and measure the magnetic signals from elements of the same species in nonequivalent atomic environments, i.e., to separate magnetic signals not only by element type, but also by the type of environment. This inventive x-ray detection and analysis technique uses circularly polarized x-rays to study magnetism in crystals with unprecedented resolution power. The technique combines x-ray diffraction from crystals with the elemental magnetic fingerprints obtained near x-ray absorption edges to yield element and site-specific magnetic data. Specifically; this invention functions by combining knowledge from crystallography and by manipulating the polarization of x-rays, the energy of which is tuned near element-specific electronic excitations. Site separation is achieved by the proper choice of diffraction conditions and magnetic sensitivity is obtained by measuring the contrast in diffracted intensity for opposite helicities of circularly polarized x-rays. Proof of principle studies have been carried out on $Nd_2Fe_{14}B$ (the best permanent magnet composition presently available) with good success.

This invention is directed to apparatus for determining the magnetic characteristics of a magnetic material, the apparatus comprising: a phase retarder for converting a linearly polarized incident x-ray beam to a circularly polarized x-ray beam which alternates between left-handed (LH) and right-handed (RH) helicity at a given frequency and has energy selected to interact with a designated species of atoms in the magnetic material; a first detector that measures the intensity of the circularly polarized x-rays incident on the magnetic material, wherein the incident photons are diffracted by atoms located at selected sites in the magnetic material to provide diffracted photons; a second detector for detecting the diffracted photons; and a counter coupled to the first and second detectors for counting and comparing the number of incident and diffracted photons for each left- and right-helicity, and providing an output signal representing the magnetic characteristics of a designated species of atoms at selected sites in the magnetic material.

BRIEF DESCRIPTION OF THE DRAWINGS

The appended claims set forth those novel features which characterize the invention. However, the invention itself, as well as further objects and advantages thereof, will best be understood by reference to the following detailed description of a preferred embodiment taken in conjunction with the accompanying drawings, where like reference characteristics identify like elements throughout the various figures, in which:

DETAILED DESCRIPTION OF PREFERRED EMBODIMENTS

The ability of x-ray-based techniques to separate magnetic contributions from different elements in heterogeneous samples is one of the most important advantages of x-rays over neutrons when probing magnetism. X-ray magnetic circular dichroism (XMCD) achieves this separation by tuning the x-ray energy to element-specific electron excitations whose absorption cross section depends on x-ray helicity (left or right). This dichroism arises from an imbalance between the spin-up and spin-down density of electronic states near the Fermi energy, which is characteristic of ferro (ferri) magnetic materials. While x-ray dichroism is commonly measured in absorption, a related dichroic effect occurs in the resonant scattering/diffraction of circularly polarized x-rays, where the virtual photoelectron is sensitive to that same spin imbalance in the intermediate state. Analog lock-in detection of XMCD in the absorption channel is already available at the X-ray Operations and Research Sector 4 of the Advanced Photon Source at Argonne National Laboratory, Argonne, Ill. Now, a digital lock-in detection scheme in accordance with the present invention has been developed for measurements of dichroic scattering/diffraction.

Advantages of dichroic scattering/diffraction include the ability to exploit structural factor effects in crystals in order to separate magnetic contributions from elements of the same species in nonequivalent crystal sites, to determine element-specific magnetization depth profiles in films and multilayers, and to separate magnetic signals from the same element in dissimilar crystal phases in multiphase materials such as nanocomposites.

Figure 1:
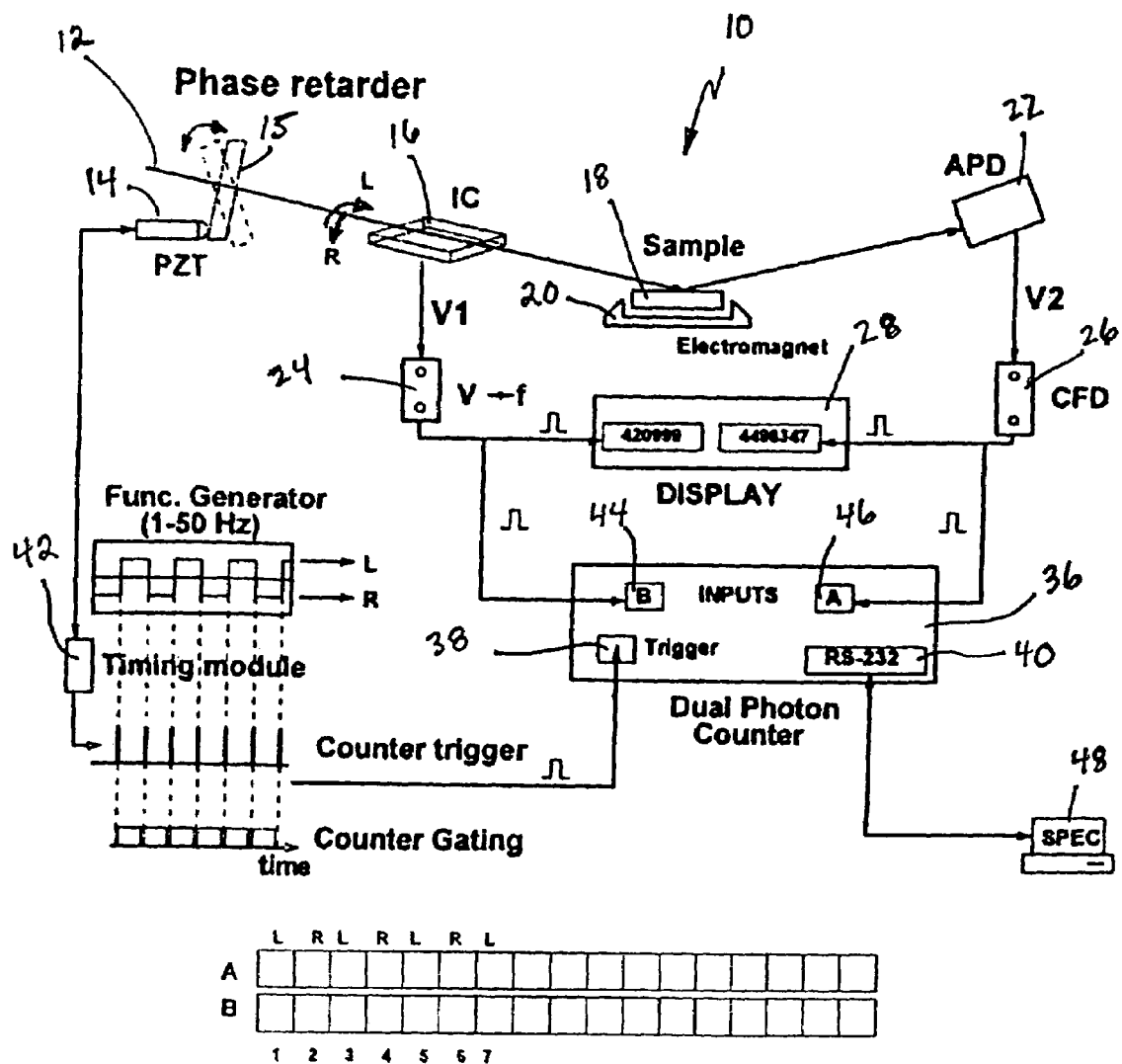
FIG. 1 is a simplified schematic diagram of a digital lock-in detection system for detecting and measuring the dichroic diffraction of circularly polarized x-rays in magnetic materials in accordance with the present invention.

The inventive detection system shown in FIG. 1 permits measurement of the x-ray-diffracted intensity to be synchronized with the helicity modulation of a circularly polarized incoming x-ray beam, which alternates in the 1- to 50-Hz range. A square wave with half-duty cycle expands/contracts a piezoelectric actuator causing a phase-retarding optical element to yield opposite helicities of circular polarized x-rays. Upon helicity switching, a timing module triggers incident and scattered intensity scalers of a dual photon counter for a time interval (gating) just below the half period of the square wave. This allows measurement of incident and scattered x-ray beam intensities for opposite helicites to be performed over many helicity switchings in a short time, with the data for each type of helicity stored in even and odd addresses, respectively, of the photon counter's memory arrays. This detection scheme, coupled to a fast-counting avalanche photodiode detector, yields large improvements in signal-to-noise ratios and a reduction of systematic errors over conventional detection approaches, wherein beam helicity is switched only once.

Figure 2:
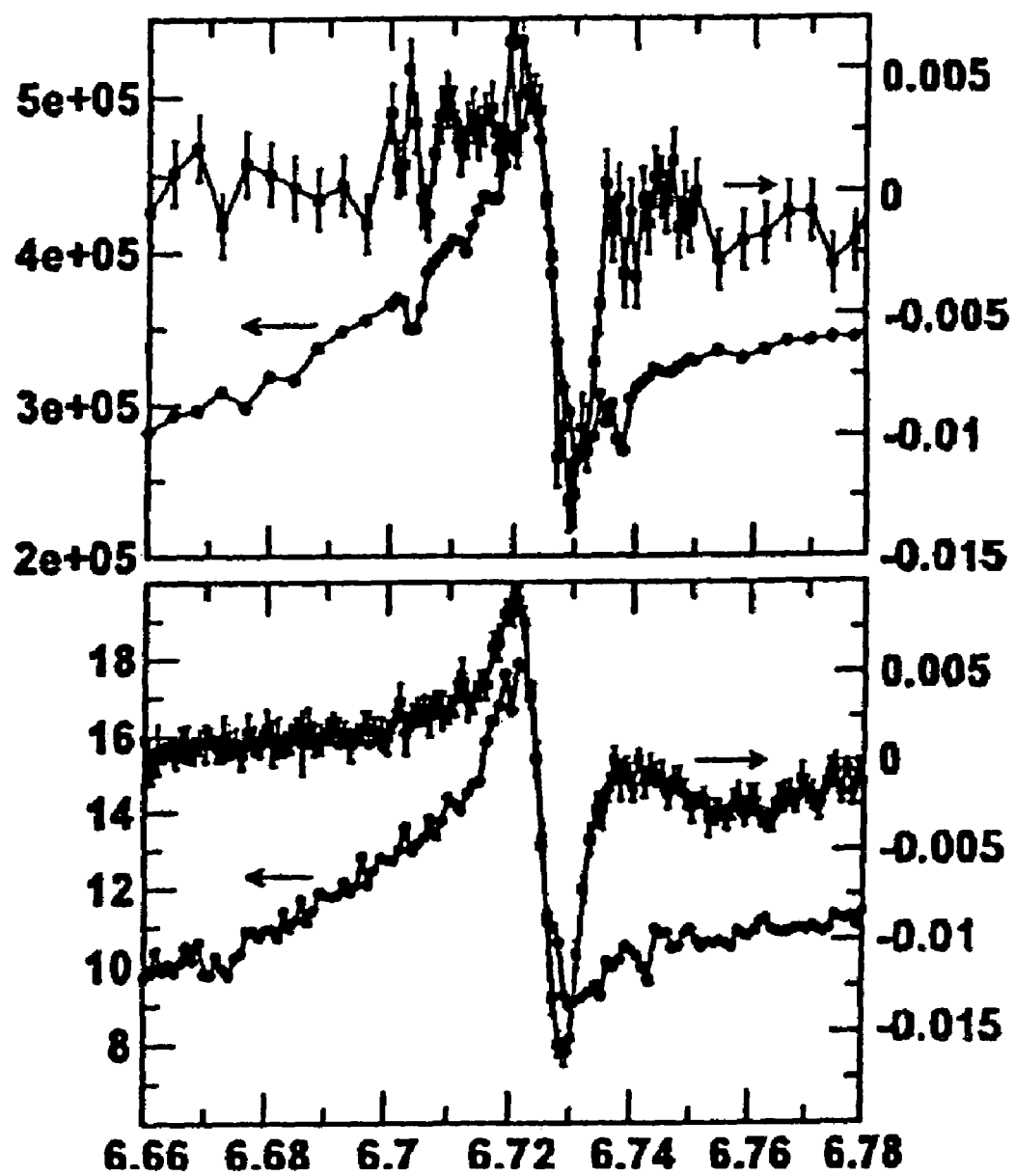
FIG. 2 is a graphic comparison of the detection of circularly polarized x-rays dichroically diffracted from magnetic materials in the prior art with the detection provided by the digital lock-in detection system of the present invention.

FIG. 2 compares data collected by using a conventional method (top) to that collected by using digital lock-in over 20 cycles of helicity switching in accordance with the present invention. In addition to improvements in data quality, the lock-in measurement was done in half the time of the conventional measurement. This development extends the detectability of dichroic scattering/diffraction to 1 part in 10,000. This level of sensitivity is particularly suited for detection of dichroic diffraction from single crystals and small-angle dichroic reflectivity/scattering from layered nanostructures.

Referring to FIG. 1, there is shown a simplified schematic diagram of a digital lock-in detection system 10 for detecting and measuring the magnetic characteristics of a magnetic material in accordance of the principles with the present invention. The digital lock-in detection system 10 includes a phase retarder comprised of the combination of a piezoelectric actuator 14 and a phase retarding optical element 15 through which an incident linearly polarized x-ray beam 12 is directed. A timing module 42 provides a square wave input to the piezoelectric actuator 14 for modulating the phase retarding optical element 15, with the square wave input alternating in the 1- to 50-Hz range. The square wave input signal with a half-duty cycle expands and contracts the piezoelectric actuator 15 causing the phase retarding optical element 15 to provide a circularly polarized x-ray beam output having opposite helicities of the circularly polarized x-rays. The opposite helicities of the circularly polarized x-rays are provided to an ionization chamber 16 which includes an ionizing gas across which a high voltage is applied. The incident photons knock off electrons from the gas atoms, with the number of electrons collected being proportional to the number of photons. Ionization chamber 16 thus provides for the detection of the number of photons transmitted through the phase retarding optical element 15 which is a measure of the intensity of the incident circularly polarized x-ray beam 12. The phase retarding optical element 15 is preferably a single crystal diamond capable of changing the helicity of the circular polarized incident x-ray beam 12.

A voltage generated in the ionization chamber 16 in response to the dual helicity x-ray beam is directed to a voltage-to-frequency converter 24, while the x-ray beam is directed onto a magnetic sample 18. Disposed adjacent the magnetic sample 18 is an electromagnet 20 for aligning the magnetization of the magnetic sample along a predetermined direction established as a reference by the magnetic field of the electromagnet 20. An avalanche photodiode detector 22 outputs a voltage pulse to a constant fraction discriminator 26, where the voltage pulses are converted to logic pulses at a frequency corresponding to the rate at which photons are scattered by the magnetic sample 18 and collected by the avalanche photodiode detector 22. The output of the ionization chamber 16 to the voltage-to-frequency converter 24 is also a voltage and a measure of the number of photons with dual-helicity incident upon the magnetic sample 18. The frequency signals from voltage converter 24 and constant fraction discriminator 26 are provided to a display device 28 in order to provide a visual comparison of the signal output by the ionization chamber 16 and the avalanche photodiode 22.

The outputs from voltage converter 24 and constant fraction discriminator 26 are also respectively provided to an incident beam intensity scaler 44 and a scattered beam intensity scaler 46 of a dual photon counter 36. The incident beam intensity scaler 44 and the scattered beam intensity scaler 46 open and close in a synchronized manner with the modulation in x-ray beam helicity. As such, they operate as filters to reject signals which do not have the same frequency as the input signal to the piezoelectric actuator 14 which modulates the phase retarding optical element 15. The timing module 42 which provides the square wave input to the piezoelectric actuator 14 also provides a pulsed signal to a trigger circuit 38 within the dual photon counter 36 for insuring that the counter detects only signals at the operating frequency of the phase retarder. As shown in FIG. 1, the half wave pulses output by the timing module 42 are synchronized with its trigger pulse output to the trigger circuit 38. The dual photon counter 36 includes an RS 232 interface for communicating with a computer controller 48 responsive to control inputs such as from a system operator. The computer controller 48 might be in the form of a PC or a laptop computer.

Below the schematic diagram in FIG. 1, there is shown a simplified schematic arrangement for the collection of helicity data for the incident and scattered beams. In row "A", which is a representation of scaler 44, plural spaced bins are provided for counting incident intensities of left ("L") and right ("R") helicity photons over time, such as over ten seconds. The lower row labeled "B", which is a representation of scaler 46, is used for counting scattered photons detected by the avalanche photodiode 22 for the same timing sequence (and hence helicity sequence) as in row "A" and the two are directly compared. The data stored in these scalers is read by the computer controller 48 via a RS 232 serial interface 40.

Referring to FIG. 2, there is shown a graphic comparison between measurements as made by a prior art approach and measurements made by the digital lock-in detection system 10 of the present invention. The upper graph shows conventional detection results using a scintillator detector. The lower graph shows detection using the digital lock-in detector system 10 of the present invention over 20 cycles of helicity switching using an avalanche photodiode as previously described. In addition to improvements in measured data quality as shown by comparing the upper and lower curves in FIG. 2, the lock-in measurement in accordance with the present invention was done in half the time of the conventional measurement shown in the upper graph. This improvement extends the detectability of dichroic scattering/diffraction data to 1 part in 10,000. The digital lock-in detection system 10 of the present invention is particularly suited for detection of dichroic diffraction from single crystals and small angle dichroic reflectivity-scattering from layered nanostructures.

The present invention was used in the analysis of $Nd_2Fe_{14}B$, the best permanent magnet material currently available. Analysis of this magnetic material using the present invention showed that only one of the two dissimilar Nd sites is responsible for the magnetic stability of this material. Unexpectedly, the other site acts to reduce magnetic stability. Knowledge such as this is critical in designing future materials with specific desired magnetic properties. The present invention is also particularly adapted for the study of magnetic nanocomposites (i.e., mixtures of magnetically hard and soft materials at the nanoscale) as well as to the study of magnetic thin films. The present invention can also be used to measure magnetization depth profiles near interfaces between magnetic thin films, which are intimately related to the performance of thin film magnetic devices such as read heads in computer hard discs and spintronics devices such as magnetic random access memories.

While particular embodiments of the present invention have been shown and described, it will be obvious to those skilled in the relevant arts that changes and modifications may be made without departing from the invention in its broader aspects. Therefore, the aim in the appended claims is to cover all such changes and modifications as fall within the true spirit and scope of the invention. The matter set forth in the foregoing description and accompanying drawings is offered by way of illustration only and not as a limitation. The actual scope of the invention is intended to be defined in the following claims when viewed in their proper perspective based on the prior art.

We claim:

1. Apparatus for determining the magnetic characteristics of a magnetic material, the apparatus comprising:
a phase retarder for converting a linearly polarized incident x-ray beam to a circularly polarized x-ray beam, wherein said circularly polarized x-ray beam alternates between left-handed (LH) and right-handed (RH) helicity at a given frequency and has energy selected to interact with a designated species of atoms in the magnetic material;
a first detector for measuring the intensity of the circularly polarized x-ray beam incident on the magnetic material, wherein the circularly polarized x-ray beam is diffracted by atoms located at selected sites in the magnetic material to provide a diffracted beam;
a second detector for detecting the diffracted beam; and
a counter coupled to said first and second detectors for counting and comparing the intensities of the incident and diffracted x-ray beams having left-and-right-helicities, and providing an output signal representing the magnetic characteristics of a designated species of atoms at selected sites in the magnetic material.

2. The apparatus of claim 1 wherein said phase retarder includes, in combination, a piezoelectric actuator and a phase retarding optical element for providing the circularly polarized x-ray beam.

3. The apparatus of claim 2 wherein said phase retarding optical element is a single crystal diamond.

4. The apparatus of claim 2 wherein a square wave input with a half duty cycle is provided to said piezoelectric actuator for oscillating said phase retarding optical element and switching the helicity of the circularly polarized incident x-ray beam at said given frequency.

5. The apparatus of claim 4 wherein the helicity of the circularly polarized incident x-ray beam is switched in a range of 1-50 Hz.

6. The apparatus of claim 1 wherein said first detector comprises an ionization chamber.

7. The apparatus of claim 1 further comprising an electromagnet disposed adjacent the magnetic material for providing a reference magnetic field at the location of the magnetic material.

8. The apparatus of claim 1 wherein said second detector for detecting said diffracted x-ray beam comprises a photodiode.

9. The apparatus of claim 8 wherein said photodiode comprises an avalanche photodiode.

10. The apparatus of claim 1 further comprising a digital display coupled to said first and second detectors for providing a visual display of the intensity of the incident and diffracted x-ray beams.

11. The apparatus of claim 1 further comprising a constant fraction discriminator coupled to said second detector and to said counter for accurately detecting the arrival of the diffracted x-ray beam onto the second detector.

12. The apparatus of claim 11 wherein said counter comprises a dual photon counter for counting and comparing incident and diffracted x-ray beams and further comprises a trigger circuit for actuating the dual photon counter at said given frequency for removing system-related inaccuracies in determining the magnetic characteristics of the magnetic material.

13. The apparatus of claim 12 further comprising a timing circuit for providing first timed pulses to said trigger circuit for actuating said dual photon counter at selected time intervals.

14. The apparatus of claim 13 wherein said timing circuit further provides said first timed pulses to said phase retarder for converting the linearly polarized incident x-ray beam to the circularly polarized x-ray beam.

15. The apparatus of claim 1 further comprising a computer controller coupled to said dual photon counter for allowing an operator to control the operation of the apparatus.

16. Apparatus for determining the magnetic characteristics of a magnetic material, said apparatus comprising:
- a phase retarder for converting a linearly polarized incident x-ray beam to a circularly polarized x-ray beam having energy selected to interact with a designated species of atoms in the magnetic material;
- a first detector for measuring the intensity of the incident x-ray beam;
- a timing module coupled to said phase retarder for providing a first square wave input with a half duty cycle to said phase retarder for switching the circularly polarized incident x-ray beam between left-handed (LH) and right-handed helicity at a given frequency;
- means for directing the circularly polarized x-ray beam onto the magnetic material, wherein said circularly polarized x-ray beam is diffracted by atoms located at selected sites in the magnetic material to provide a diffracted x-ray beam;
- a second detector for measuring the intensity of the diffracted x-ray beam; and
- a dual photon counter coupled to said first and second detectors for comparing the intensities of the incident and diffracted x-ray beams for providing an output signal representing the magnetic characteristics of a designated species of atoms at selected sites in the magnetic material, wherein said dual photon counter is actuated at said given frequency for removing system-related inaccuracies in determining the magnetic characteristics of the magnetic material.

* * * * *